United States Patent [19]

Kawaguchi et al.

[11] Patent Number: 5,545,747
[45] Date of Patent: Aug. 13, 1996

[54] CYCLOBUTANECARBOXYLIC ACID DERIVATIVES AND LIQUID CRYSTALLINE COMPOSITIONS CONTAINING THEM

[75] Inventors: Megumi Kawaguchi; Hiromi Inoue; Atsushi Sugiura; Kenji Suzuki; Tsunenori Fujii, all of Soka, Japan

[73] Assignee: Kanto Kagaku Kabushiki Kaisha, Tokyo, Japan

[21] Appl. No.: 283,755

[22] Filed: Aug. 1, 1994

Related U.S. Application Data

[63] Continuation of Ser. No. 848,000, Apr. 16, 1992, abandoned.

[30] Foreign Application Priority Data

Aug. 16, 1990 [JP] Japan .................. 2-215045

[51] Int. Cl.⁶ .................................. C07C 69/74
[52] U.S. Cl. ........................... 560/123; 252/299.63
[58] Field of Search ........................... 560/123

[56] References Cited

U.S. PATENT DOCUMENTS

| | | | |
|---|---|---|---|
| 3,673,237 | 6/1972 | Janiak | 560/123 |
| 4,795,579 | 1/1989 | Vauchier | 560/1 |
| 5,045,229 | 9/1991 | Bartmann | 252/299.01 |
| 5,188,759 | 2/1993 | Bartmann | 252/299.01 |
| 5,262,085 | 11/1993 | Bartmann | 252/299.61 |
| 5,308,537 | 5/1994 | Coates | 252/299.60 |
| 5,389,291 | 2/1995 | Reiffenrath | 252/299.61 |

FOREIGN PATENT DOCUMENTS

| | | |
|---|---|---|
| 62-201843 | 9/1987 | Japan . |
| 62-01843 | 9/1987 | Japan . |
| 1-075448 | 3/1989 | Japan . |
| 1207254 | 8/1989 | Japan . |
| 1-299258 | 12/1989 | Japan . |
| 2169537 | 6/1990 | Japan . |
| 2174747 | 7/1990 | Japan . |

OTHER PUBLICATIONS

"Kirk–Othmer Encyclopedia of Chemical Technology," vol. 14, 3rd Ed., pp. 395–427 (1981).
"Submicrosecond Bistable Electro–Optic Switching in Liquid Crystal" Appl. Phys. Lett 361(11), 1 Jun. 1980–pp. 899–901 Ferroelectric Liquid Crystal Tome 36, Mars 1975, pp. L–69–L–71.
N. Clark et al., Appl. Phys. Lett. 36 (11), (1980), pp. 899–901 Submicrosecond bistable electro–optic switching in liquid crystals.
R. B. Meyer et al., "Ferroelectric liquid crystals", Le Journal de Physique, (1975), pp. L–69–L–71, vol. 36.

Primary Examiner—Michael L. Shippen
Attorney, Agent, or Firm—Birch, Stewart, Kolasch & Birch, LLP

[57] ABSTRACT

An optically inactive cyclobutanecarboxylic acid derivative of the general formula

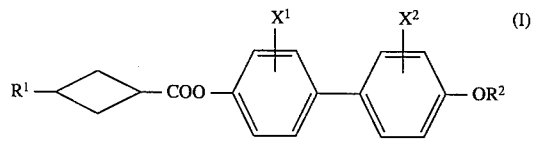

wherein $R^1$ is a hydrogen atom or a straight or branched chain alkyl group having 1–14 carbon atoms, $R^2$ is a straight or branched chain alkyl group having 1–14 carbon atoms, $X^1$ and $X^2$ independently represent hydrogen or fluorine atoms, as well as a liquid crystalline composition containing at least one such derivative.

19 Claims, No Drawings

CYCLOBUTANECARBOXYLIC ACID DERIVATIVES AND LIQUID CRYSTALLINE COMPOSITIONS CONTAINING THEM

This application is a continuation of application Ser. No. 07/848,000 filed on Apr. 16, 1992, now abandoned.

TECHNICAL FIELD

The present invention relates to new liquid crystalline compounds as well as liquid crystalline compositions containing at least one of the liquid crystalline compounds. More particularly, the present invention relates to ferroelectric liquid crystals and to new liquid crystalline compositions having a cyclobutane ring which are useful as components for preparing practical ferroelectric liquid crystalline compositions and excellent in chemical stability as well as to liquid crystalline compositions containing at least one of the new liquid crystalline compounds having a cyclobutane ring.

BACKGROUND OF THE INVENTION

Liquid crystal display elements are widely used as display elements for watches, electronic desk-top computers, personal word processors, pocket-size TV sets, etc. This stems from the fact that they have such beneficial characteristics as no eyestrain because of their passive device, low electric power consumption, a thin structure etc. However, they are restricted in their practical applications because of different problems such as slow response and lack of memory effect.

In an attempt to expand their areas of application there has been found, for example, the super twisted nematic (STN) display system, which is an improvement of the twisted nematic (TN) display system. These systems, however, are not sufficient for large screen or graphic display use. Various studies have therefore been made of liquid crystal display elements which can supersede them.

One such display system [N. A. Clark et al., Applied Phys. lett., 36, 899 (1980)] utilizes ferroelectric liquid crystals [R. B. Meyer et al., J. de. Phys., 36 L-69 (1975)]. Because of its advantageous characteristics such as fast response, which is 100 times as fast as that of conventional systems, and memory effect, it is expected to expand areas of application of liquid crystal display elements. The term "ferroelectric liquid crystal" is used to mean a series of smectic liquid crystals whose molecular longitudinal axis is at a certain angle to the normal of the layer, but in practice the chiral smectic C (SmC*) phase is utilized.

Ferroelectric liquid crystals for preparing display elements are used in the form of (1) a liquid crystalline composition Obtained by blending together different compounds with the SmC* phase or (2) a liquid crystalline composition obtained by blending different compounds having the SmC phase with optically active compounds. Early research and development of ferroelectric liquid crystal display elements used liquid crystalline compositions of the formulation in accordance with (1) above. Since, with the advent of further research and development, addition of optically active compounds was found to result in the formation of ferroelectric crystals, however, the tendency is for compositions of the formulation in accordance with (2) above to be used more. This is because the formulation in accordance with (2) above is considered to be more advantageous in practical applications, for example in that it renders easier the adjustment of different properties demanded in the market (e.g. operating temperature range, response time, spontaneous polarization, helical pitch, chemical stability etc.) and the synthesis of SmC compounds is less expensive than that of SmC* compounds.

Even the formulation in accordance with (2) above, have yet to reach a stage of providing compositions having sufficient properties for putting into practical use, there thus now being a need for a variety of compounds useful as components with which to prepare ferroelectric liquid crystalline compositions being developed.

SUMMARY OF THE INVENTION

The present inventors, aiming at the creation of compounds having necessary SmC phase for the preparation of ferroelectric liquid crystalline compositions, have extensively studied compounds of different new structures by designing, synthesizing and evaluating them, in particular based on the idea that in the case of heretofore known compounds the SmC phase temperature range is seldom close to room temperature or is narrow albeit close thereto and the presence of many benzene rings and benzoic acid ester-type structures in their substance structure results in higher viscosities thus being disadvantageous in terms of attaining a high speed response. As a result the present inventors have succeeded in synthesizing new compounds which show a wide SmC phase temperature in the vicinity of room temperature as well as chemical stability and which give, when mixed together, mixtures of low viscosity.

DETAILED DESCRIPTION OF THE INVENTION

The present invention provides optically inactive cyclobutanecarboxylic acid derivatives of the general formula

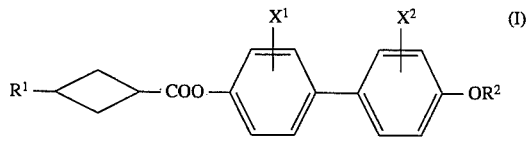

wherein $R^1$ is a hydrogen atom or a straight or branched chain alkyl group having 1–14 carbon atoms, $R^2$ is a straight or branched chain alkyl group having 1–14 carbon atoms, $X^1$ and $X^2$ independently represent hydrogen or fluorine atoms, and

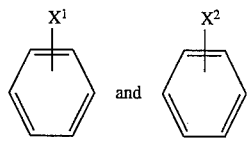

independently represent 1,4-phenylene, monofluoro-substituted 1,4-phenylene or difluoro-substituted 1,4-phenylene, as well as liquid crystalline compositions characterized by containing at least one of the compounds.

The new liquid crystalline compounds according to the present invention show, even when used individually, the SmC phase over a wide temperature range in the vicinity of room temperature, and can be mixed together in appropriate proportions to prepare mixtures having a wider temperature range for the SmC phase. Furthermore, compositions obtained by addition of appropriate optically active compounds to such compounds show an optical response upon application of a voltage. Accordingly, the new compounds according to the present invention are extremely useful as components in the preparation of ferroelectric liquid crystalline compositions of practical use.

Synthetic routes for the compounds of the present invention will now be described below and the present invention will then be explained in more detail by way of working examples etc.

In the following are shown synthetic routes using reaction equations, which, are for illustrative purposes only and in no way restrict the present invention by no to the case with working examples.

Synthetic route (1)

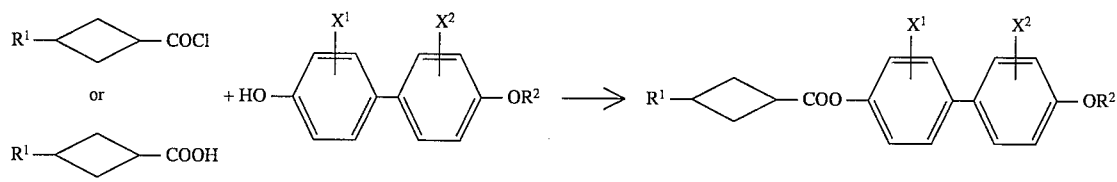

Synthetic route (2)

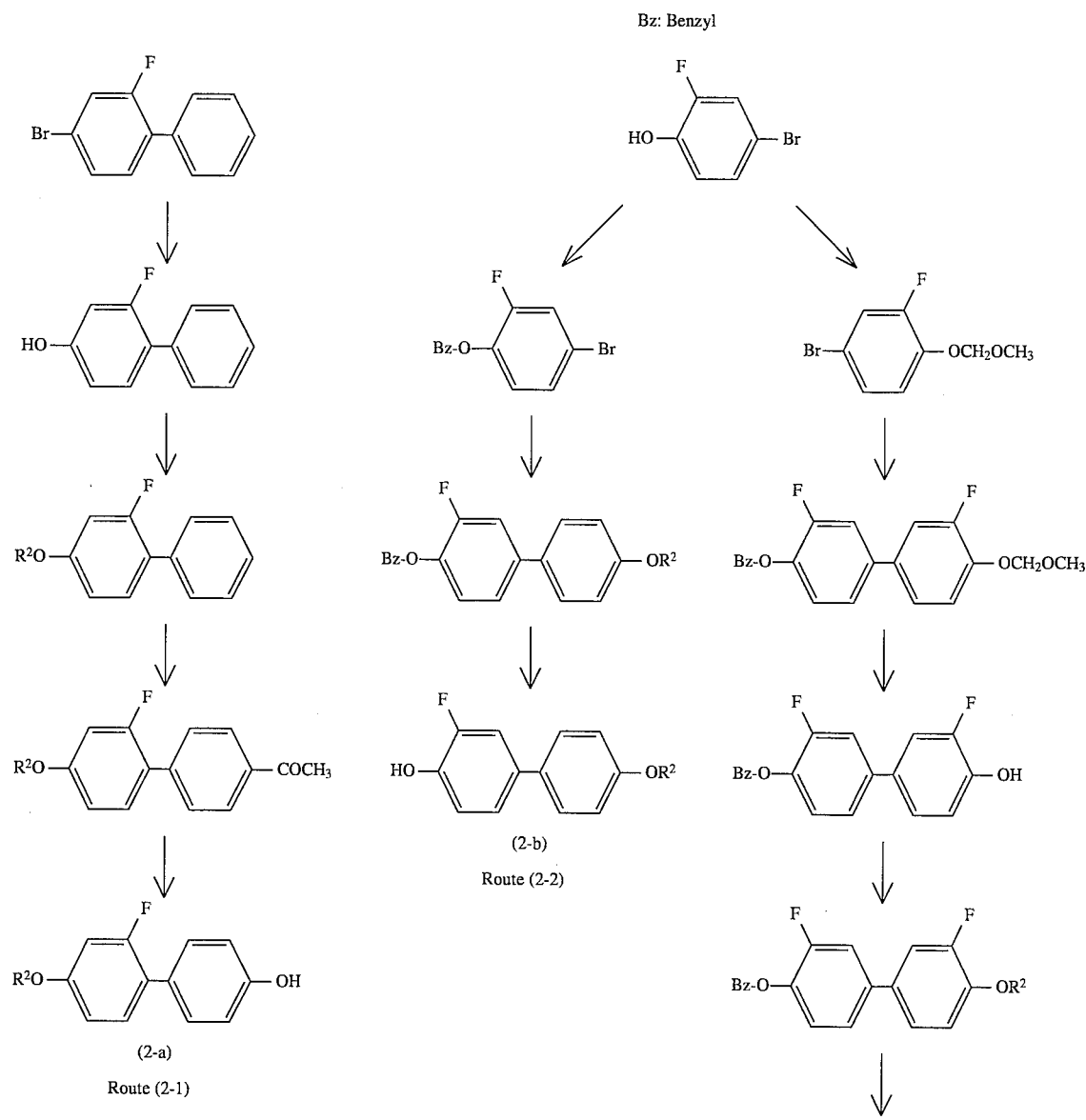

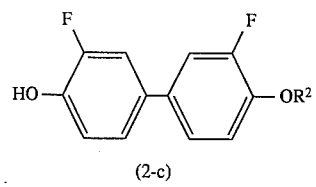
(2-c)

Route (2-3)

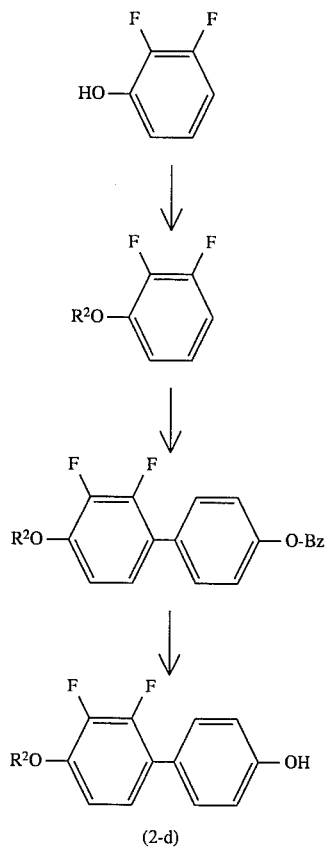

(2-d)

Route (2-4)

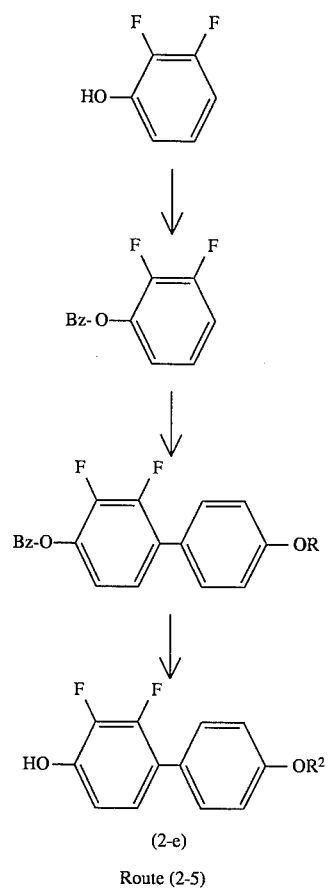

(2-e)

Route (2-5)

The synthetic routes shown above will now be described in detail below.

Cyclobutanecarboxylic acid derivatives of the general formula (I) can be synthesized, in accordance with synthetic route (1), by conventional esterification by reacting a compound of the formula

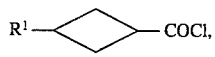

in the presence of pyridine, with a compound of the formula

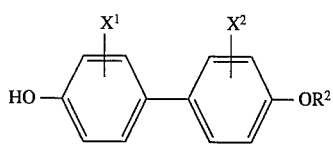

or reacting a compound of the formula

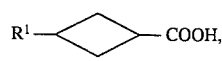

in the presence of DCC, with a compound of the formula

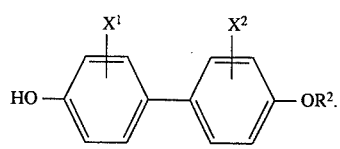

The compounds of the formula $R^1$—◇—COOH used herein may be obtained by the method disclosed in Japanese unexamined patent application publication No. 62-201843 (JP, A, 62-201843), and compounds of the formula

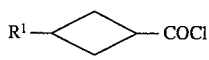

may be synthesized, in accordance with the conventional method for the synthesis of acid chlorides, by reacting a compound of the formula

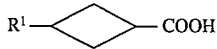

with thionyl chloride. On the other hand, compounds of the formula

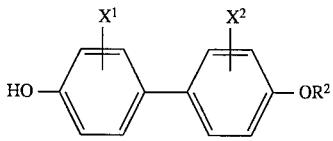

wherein $X^1$ and $X^2$ are all hydrogen atoms are commercially available, and fluoro-compounds of the formula

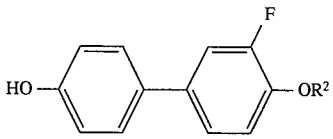

or

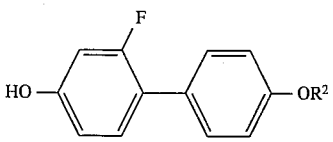

may be synthesized by methods disclosed in Japanese unexamined patent application publication No. 2-169537 (JP, A, 2-169537) and Japanese unexamined patent application publication No. 2-174747 (JP, A, 2-174747). Compounds of the other formula

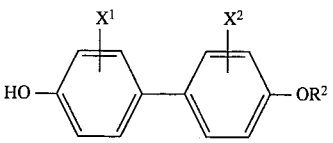

may be synthesized in accordance with synthetic route (2). Thus in route (2-1), 2-fluoro-4-bromobiphenyl is reacted with magnesium to prepare Grignard reagent, which is subjected to reaction with tributyl borate and then to acidic hydrolysis to obtain 2-fluoro-4-hydroxybiphenyl. The product is etherified with alkyl bromide to give 2-fluoro-4-alkoxybiphenyl, which is then acetylated by the Friedel-Crafts reaction to give 2-fluoro-4-alkoxy-4'-acetylbiphenyl. The product is subjected to Baeyer-Villiger oxidation and then to hydrolysis to give compound of the formula

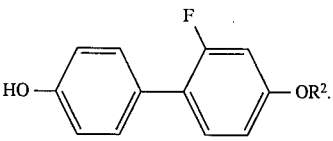
(2-a)

In route (2-2), Grignard reagent is prepared from magnesium and 3-fluoro-4-benzyloxy-bromobenzene obtained by etherification of 3-fluoro-4-hydroxy-bromobenzene with benzyl chloride, and then subjected to cross-coupling reaction with 4-alkoxy-bromobenzene to give 3-fluoro-4-benzyloxy- 4'-alkoxybiphenyl. The product is subjected to reaction with hydrogen under pressure for benzyl ether cleavage, using Pd-C as catalyst, whereby compound of the formula

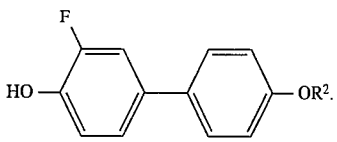
(2-b)

In route (2-3), reactions are carried out following the same manner as in route (2-2), except in that 3-fluoro- 4-alkoxy-bromobenzene is used in place of the 4-alkoxy-bromobenzene in route (2-2). Alternatively, 3-fluoro-4-hydroxy-bromobenzene is etherified with chloromethyl methyl ether and the product is subjected to coupling reaction with 3-fluoro-4-benzyloxybromobenzene, then to demethoxymethylation and again to etherification with alkyl bromide, to give 3,3'-difluoro-4-benzyloxy-4'-alkoxybiphenyl, which upon debenzylation gives compound of the formula

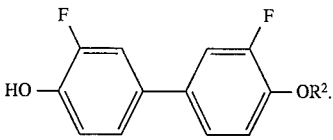
(2-c)

In route (2-4), 2,3-difluoro-alkoxybenzene, which is obtained by etherifying 2,3-difluorophenol with alkyl bromide, is lithiated with butyl lithium and the product is subjected to coupling reaction with 4-bromophenyl benzyl ether obtained by etherification of 4-bromophenol with benzyl chloride. The thus obtained 2,3-difluoro-4-alkoxy-4'-benzyloxybiphenyl is hydrogenated under pressure in the presence of Pd-C catalyst for benzyl ether cleavage, whereby compound of the formula

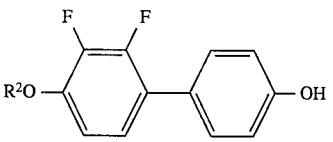
(2-d)

is obtained.

In route (2-5), compound of the formula

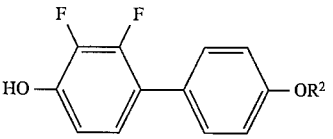
(2-e)

can be obtained by carrying out reactions following the same manner as in route (2-4) except in that benzyl chloride is used in place of the alkyl bromide, and that alkyl bromide is used in place of the benzyl chloride.

Cis or trans form of compounds of the general formula (I) may be obtained by separation and purification from mixtures of both forms using preparative chromatography. Alternatively, compound of the formula

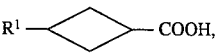

which can be obtained by the method disclosed in TOKKAI-Sho 62-201843 (Japanese unexamined patent application publication No. 201843/'87), is esterified with a phenol, e.g. with

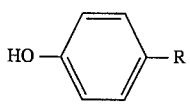

wherein R is an alkyl or alkoxy group to give compound of

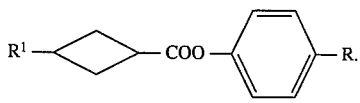

The compound is then separated by preparative chromatography into its cis and trans forms, and the respective forms are subjected to ester hydrolysis followed by purification to give cis and trans forms, respectively, of carboxylic acid of the formula

The respective forms, when used as starting material in synthetic route (1), will give cis and trans forms of compound of the general formula (I).

In the following will now be shown working examples to further illustrate the present invention.

The notations and abbreviations used throughout the description including working examples have the following meanings:

| | |
|---|---|
| GLC: | gas chromatography |
| HPLC: | high performance liquid chromatography |
| IR: | infra-red absorption spectroscopy |
| Mass: | mass spectrometry |
| m.p.: | melting point |
| b.p.: | boiling point |
| C: | cystals |
| C': | crystals different from C |
| Sx: | unidentified smectic phase |
| $S_B$: | smectic B phase |
| SmC, Sc: | smectic C phase |
| SmC*, Sc*: | chiral smectic C phase |
| $S_A$: | smectic A phase |
| Ch: | cholesteric phase |
| Ne: | nematic phase |
| I: | isotropic liquid |
| ?: | temperature being indefinite |

EXAMPLE 1

(a) Synthesis of

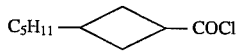

A reaction vessel was charged with 140 g of thionyl chloride and 100 ml of benzene, and 100 g of 3-pentylcyclobutanecarboxylic acid was added dropwise under reflux with stirring. The resultant mixture was refluxed with stirring for 8 hours and the excess thionyl chloride was azeotropically distilled off with benzene and the residue was distilled under reduced pressure to obtain 101 g (yield 91%) of 3-pentylcyclobutanecarboxylic acid chloride.

GLC 99% or more
b.p. 113.5° C./17 mmHg (b) Synthesis of

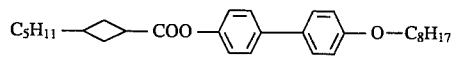

A reaction vessel was charged with 7 g of 4-hydroxy-4'-octyloxybiphenyl, 2 g of pyridine and 50 ml of benzene, and 5 g of the 3-pentylcyclobutanecarboxylic acid chloride obtained in (a) above was added dropwise with stirring at 60° C. The resultant mixture was refluxed with stirring for 5 hours. The reaction liquid was poured into water and the benzene layer was washed with water and dried over Glauber's salt. The benzene was distilled off and the residue was purified by way of column chromatography on silica gel (eluent: hexane/benzene = 3/1) to obtain 10 g (yield 95%) of 4-octyloxybiphenyl-4'-yl 3-pentylcyclobutanecarboxylate.

The purity of the product was at least 99% by HPLC and TLC showed only one spot. The resultant substance was confirmed to be the end product in view of its measurement by IR and its molecular ion peak found at 450 by Mass and also in view of the starting materials used.

This product was inserted into a Mettler hot stage FP-82 and its phase transition was observed under a polarization microscope. A result of the observation is shown in Table 1.

EXAMPLE 2

Synthesis of

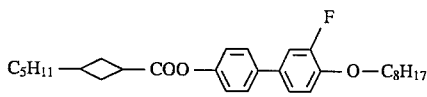

Except that 7.4 g of 3-fluoro-4-octyloxy-4'-hydroxybiphenyl was used in place of 7 g of the 4-hydroxy 4'-octyloxybiphenyl used in Example 1-(b) and purification carried out by column chromatography on silica gel (hexane/benzene= 2/1), the operation was performed in the same manner as in Example 1-(b) to obtain 5.2 g (yield 47.7%) of 3-fluoro-4-octyloxybiphenyl-4'-yl 3-pentylcyclobutanecarboxylate.

The purity of this product was at least 99% by HPLC and TLC showed only one spot. The resultant substance was confirmed to be the end product in view of its measurement by IR and its molecular ion peak found at 468 by Mass and also in view of the starting materials used.

This product was inserted into a Mettler hot stage FP-82 and its phase transition was observed under a polarization microscope. A result of the observation is shown in Table 1.

EXAMPLE 3

Synthesis of

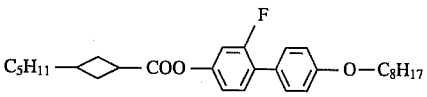

Except that 7.4 g of 4-octyloxy-2'-fluoro-4'-hydroxybiphenyl was used in place of 7 g of the 4-hydroxy- 4'-octyloxybiphenyl used in Example 1 (b) and purification carried out by column chromatography on silica gel (eluent: hexane/benzene = 1/1), the operation was performed in the same manner as in Example 1-(b) to obtain 7.5 g (yield 68.6%) of 4-octyloxy-2'-fluorobiphenyl-4'-yl 3-pentylcyclobutane carboxylate.

The purity of this product was at least 99% by HPLC and TLC showed only one spot. The resultant substance was confirmed to be the end product in view of its measurement by IR and its molecular ion peak found at 468 by Mass and also in view of the starting materials used.

This product was inserted into a Mettler hot stage FP-82 and its phase transition was observed under a polarization microscope. A result of the observation is shown in Table 1.

EXAMPLE 4

(a) Synthesis of

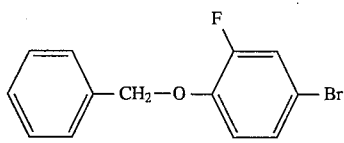

A reaction vessel was charged with 19.4 g of 2-fluoro-4-bromophenol, 12.9 g of benzyl chloride, 23.3 g of potassium carbonate and 510 ml of cyclohexanone and the reaction was carried out with stirring at 120°–140° C. for 7 hours. The reaction liquid was poured into dilute hydrochloric acid and then extracted with benzene. The benzene layer was washed with water and dried over Glauber's salt. The benzene was distilled off and the residue was purified by way of column chromatography on silica gel (eluent: hexane/benzene= 4/1) to obtain 27.9 g (yield 97.3%) of 2-fluoro-4-bromophenyl benzyl ether.

GLC 97.7%
m.p. 64.4°–66.3° C.

(b) Synthesis of

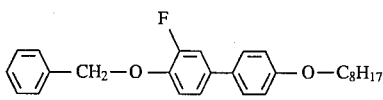

A reaction vessel was charged, under a stream of nitrogen, with 0.24 g of magnesium and a small amount of iodine. A small portion of a solution of 2.2 g of 4-octyloxy-bromobenzene in 10 ml of THF was added to and brought, while heating, into reaction with the mixture. The remainder of the THF solution was added dropwise with stirring under reflux. After completion of the dropwise addition, the mixture was refluxed with stirring for 2 hours to prepare a Grignard reagent.

Another reaction vessel was charged with 0.4 g of $Cl_2Pd(PPh_3)_2$, then under a stream of nitrogen with 2.6 ml of a 1M solution of $(iso-C_4H_9)_2AlH$ in hexane and further with a solution of 1.7 g of 2-fluoro-4-bromophenyl benzyl ether obtained in (a) above in 10 ml of THF.

The previously prepared Grignard reagent was added dropwise at 50°–60° C. to the mixture and the resultant mixture was reacted with stirring at the same temperature for 2 hours. The reaction liquid was poured into dilute hydrochloric acid and the mixture was extracted with benzene. After the extract was washed with water, the solvents were distilled off and the residue was purified by way of column chromatography on silica gel (eluent: hexane/benzene= 6/1→5/1→4/1) to obtain 0.75 g (yield 30.8%) of 3-fluoro-4-benzyloxy-4'-octyloxybiphenyl.

GLC 97.6%

(c) Synthesis of

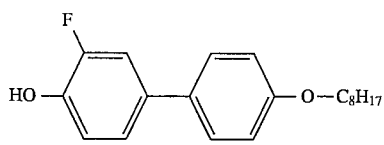

An autoclave was charged with a solution of 0.75 g of 3-fluoro-4-benzyloxy-4'-octyloxybiphenyl obtained in (b) above in 50 ml of ethyl acetate and 0.2 g of Pd/C (10%) and the atmosphere in the reaction vessel was replaced with hydrogen. The mixture was then reacted overnight with stirring at room temperature under a hydrogen pressure of 30 kg/cm$^2$. The reaction liquid was filtered to remove insolubles and the solvent was distilled off to obtain crude 3-fluoro-4-hydroxy-4'-octyloxybiphenyl. The crude product was directly used as starting material in the subsequent stage (d).

(d) Synthesis of

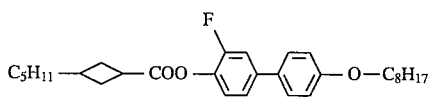

Except that the crude 3-fluoro-4-hydroxy-4'-octyloxybiphenyl obtained in (c) above was used in place of 7 g of the 4-hydroxy-4'-octyloxybiphenyl used in Example 1-(b), the amount of 3-pentylcyclobutanecarboxylic acid chloride used reduced from 5 g to 0.4 g and purification carried out by way of column chromatography on silica gel (eluent: hexane/benzene= 5/1→4/1), the operation was performed in the same manner as in Example 1-(b) to obtain 0.82 g (yield 94.7%) of 3-fluoro-4'-octyloxybiphenyl-4-yl 3-pentylcyclobutanecarboxylate.

The purity of this product was at least 99% by HPLC and TLC showed only one spot. The resultant substance was confirmed to be the end product in view of its measurement by IR and its molecular ion peak found at 468 by Mass and also in view of the starting materials used.

This product was inserted into a Mettler hot stage FP-82 and its phase transition was observed under a polarization microscope. A result of the observation is shown in Table 1.

EXAMPLE 5

(a) Synthesis of

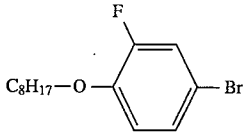

Except that 19.7 g of octyl bromide was used in place of 12.9 g of the benzyl chloride used in Example 4-(a), the operation was performed in the same manner as in Example 4-(a) to obtain 25.8 g (yield: 85.4%) of 3-fluoro-4-octyloxy-bromobenzene.

(b) Synthesis of

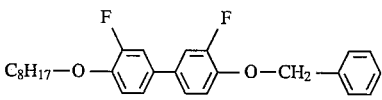

Except that 2.3 g of 3-fluoro-4-octyloxy-bromobenzene obtained in (a) above was used in place of 2.2 g of the 4-octyloxy-bromobenzene used in Example 4-(b) and purification carried out by way of column chromatography on silica gel (eluent: hexane→hexane/benzene= 20/1→10/1→8/1→6/1→5/1→4/1), the operation was performed in the same manner as in Example 4-(b) to obtain 1.44 g (yield 44.0%) of 3,3'-difluoro-4-octyloxy-4'-benzyloxybiphenyl.

GLC 98.3%

(c) Synthesis of

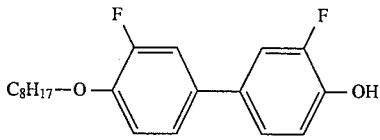

Except that 0.78 g of 3,3'-difluoro-4-benzyloxy- 4 '-octyloxybiphenyl obtained in (b) above was used in place of 0.75 g of the 3-fluoro-4-benzyloxy-4'-octyloxybiphenyl used in Example 4-(c) , the operation was performed in the same manner as in Example 4-(c) to obtain crude 3,3'-difluoro-4-octyloxy-4'-hydroxybiphenyl.

This crude product was directly used as starting material in the subsequent stage (d).

(d) Synthesis of

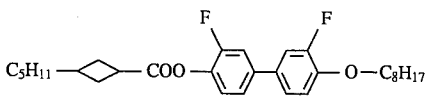

Except that the crude 3,3'-difluoro-4'-octyloxy-4-hydroxybiphenyl obtained in (c) above was used in place of 7 g of the 4-hydroxy-4'-octyloxybiphenyl used in Example 1-(b), the amount of 3-pentylcyclobutanecarboxylic acid chloride used reduced from 5 g to 0.4 g and purification carried out by way of column chromatography on silica gel (eluent: hexane/benzene= 6/1→5/1), the operation was performed in the same manner as in Example 1-(b) to obtain 0.32 g (yield 35.6%) of 3,3'-difluoro-4'-octyloxybiphenyl-4-yl 3-pentylcyclobutanecarboxylate.

The purity of this product was at least 99% by HPLC and TLC showed only one spot. The resultant substance was confirmed to be the end product in view of its measurement by IR and its molecular ion peak found at 486 by Mass and also in view of the starting materials used.

This product was inserted into a Mettler hot stage FP- 82 and its phase transition was observed under a polarization microscope. A result of the observation is shown in Table 1.

EXAMPLE 6

(a) Synthesis of

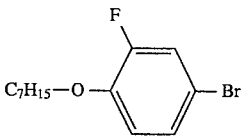

Except that 18.3 g of heptyl bromide was used in place of 12.9 g of the benzyl chloride used in Example 4-(a), the operation was performed in the same manner as in Example 4-(a) to obtain 26.6 g (yield 92.2%) of 3-fluoro-4-heptyloxybromobenzene.

b.p. 103°–107° C./0.2 mmHg (b) Synthesis of

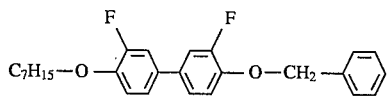

Except that 2.2 g of 3-fluoro-4-heptyloxy-bromobenzene obtained in (a) above was used in place of 2.2 g of the 4-octyloxy-bromobenzene used in Example 4-(b) and purification carried out by way of column chromatography on silica gel (eluent: hexane→hexane/benzene=8/1→6/1→4/1), the operation was performed in the same manner as in Example 4-(b) to obtain 1.66 g (yield 52.3%) of 3,3'-difluoro- 4-heptyloxy-4 '-benzyloxybiphenyl.

HPLC 99.0% m.p. 98.7°–100.1° C.

(c) Synthesis of

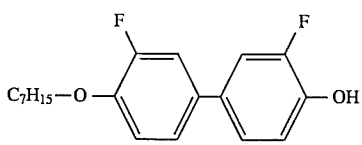

Except that 0.76 g of 3,3'-difluoro-4-benzyloxy-4'-heptyloxybiphenyl obtained in (b) above was used in place of 0.75 g of the 3-fluoro-4-benzyloxy-4'-octyloxybiphenyl used in Example 4-(c), the operation was performed in the same manner as in Example 4-(c) to obtain crude 3,3'-difluoro-4-heptyloxy-4'-hydroxybiphenyl.

The crude product was directly used as starting material in the subsequent stage (d).

(d) Synthesis of

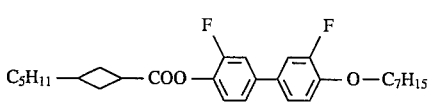

Except that the crude 3,3'-difluoro-4'-heptyloxy-4-hydroxybiphenyl obtained in (c) above was used in place of 7 g of the 4-hydroxy-4'-octyloxybiphenyl used in Example 1-(b), the amount of 3-pentylcyclobutanecarboxylic acid chloride used reduced from 5 g to 0.4 g and purification carried out by way of column chromatography on silica gel (eluent: hexane/benzene= 2/1), the operation was performed in the same manner as in Example 1-(b) to obtain 0.79 g (yield 90.5%) of 3,3'-difluoro-4'-heptyloxybiphenyl-4-yl 3-pentylcyclobutanecarboxylate.

The purity of this product was at least 99% by HPLC and TLC showed only one spot. The resultant substance was confirmed to be the end product in view of its measurement by IR and its molecular ion peak at 472 by Mass and also in view of the starting materials used.

This product was inserted into a Mettler hot stage FP- 82 and its phase transition was observed under a polarization microscope. A result of the observation was shown in Table 1.

EXAMPLE 7

(a) Synthesis of

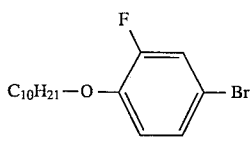

Except that 22.5 g of decyl bromide was used in place of 12.9 g of the benzyl chloride used in Example 4-(a) and purification carried out not by distillation but by chromatography on silica gel (eluent: hexane), the operation was performed in the same manner as in Example 4-(a) to obtain 30.2 g (yield 89.4%) of 3-fluoro-4-decyloxy-bromobenzene.

(b) Synthesis of

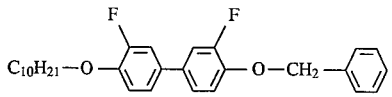

Except that 2.55 g of 3-fluoro-4-decyloxy-bromobenzene obtained in (a) above was used in place of 2.2 g of the 4-octyloxybromobenzene used in Example 4-(b) and purification carried out by way of column chromatography on silica gel (eluent: hexane→hexane/benzene= 6/1→5/1→4/1), the operation was performed in the same manner as in Example 4-(b) to obtain 1.58 g (yield 45.4%) of 3,3'-difluoro-4-decyloxy- 4'-benzyloxybiphenyl.

GLC 85.3%
m.p. 95.8°–98.6° C.

(c) Synthesis of

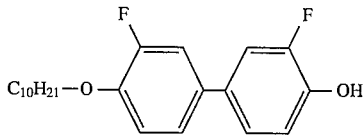

Except that 0.84 g of 3,3'-difluoro-4-benzyloxy-4'-decyloxybiphenyl obtained in (b) above was used in place of 0.75 g of the 3-fluoro-4-benzyloxy-4'-octyloxybiphenyl used in Example 4-(c), the operation was performed in the same manner as in Example 4- (c) to obtain crude 3,3 '-difluoro- 4-decyloxy- 4'-hydroxybiphenyl.

This crude product was directly used as raw material in the subsequent stage (d).

(d) Synthesis of

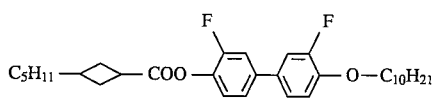

Except that the crude 3,3'-difluoro-4-decyloxy-4'-hydroxybiphenyl obtained in (c) above was used in place of 7 g of the 4-hydroxy-4'-octyloxybiphenyl used in Example 1-(b), the amount of 3-pentylcyclobutanecarboxylic acid chloride used reduced from 5 g to 0.4 g and purification carried out by way of column chromatography on silica gel (eluent: hexane/benzene= 3/1), the operation was performed in the same manner as in Example 1-(b) to obtain 0.75 g (yield 78.9%) of 3,3'-difluoro-4-decyloxybiphenyl-4'-yl 3-pentylcyclobutanecarboxylate.

The purity of this product was at least 99% by HPLC and TLC showed only one spot. The resultant substance was confirmed to be the end product in view of its measurement by IR and its molecular ion peak at 514 by Mass and also in view of the starting materials used.

This product was inserted into a Mettler hot stage FP- 82 and its transition was observed under a polarization microscope. A result of the observation is shown in Table 1.

EXAMPLE 8

Synthesis of

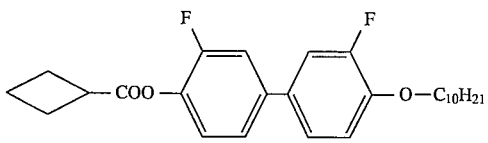

A reaction vessel was charged with 0.68 g of the crude 3,3'-difluoro-4-decyloxy-4'-hydroxybiphenyl obtained in Example 7-(c), 10 ml of methylene chloride, 0.23 g of 4-dimethylaminopyridine and 0.39 g of N,N'-dicyclohexylcarbodiimide (DCC). 0.16 g of cyclobutanecarboxylic acid was added dropwise with stirring at room temperature and the mixture was stirred overnight at the same temperature. The reaction liquid was poured into water and the methylene chloride layer was washed with dilute hydrochloric acid and then with an aqueous solution of edible salt and dried over Glauber's salt. The solvent was distilled off and the residue was purified by way of column chromatography on silica gel (eluent: hexane/benzene=3/1) to obtain 0.47 g (yield 67.4%) of 3,3'-difluoro-4-decyloxy- 4'-yl cyclobutanecarboxylate.

The purity of this product was at least 99% by HPLC and TLC showed only one spot. The resultant substance was confirmed to be the end product in view of its measurement by IR and its molecular ion peak found at 444 by Mass and also in view of the starting materials used.

This product was inserted into a Mettler hot stage FP- 82 and its phase transition was observed under a polarization microscope. A result of the observation is shown in Table 1.

EXAMPLE 9

(a) Synthesis of $C_8H_{17}$-CH(COOC$_2$H$_5$)$_2$

A reaction vessel was charged with 1 l of ethanol and 41 g of sodium was added with stirring in small portions to dissolve the same in the ethanol. 324 g of diethyl malonate was added dropwise under reflux with stirring, and the mixture was refluxed with stirring for one hour. Furthermore, 261 g of octyl bromide was added dropwise and the mixture was stirred for 5 hours.

The reaction liquid was concentrated and then poured into dilute hydrochloric acid. The mixture was extracted with benzene and the benzene extract was washed with water and dried over Glauber's salt. The solvent was distilled off and the residue was distilled under reduced pressure to obtain 314.3 g (yield 85.6%) of diethyl 2-octylmalonate.

GLC 98.3%
b.p. 108–125/0.4 mmHg (b) Synthesis of $C_8H_{17}$-CH(CH$_2$OH)$_2$

A reaction vessel was charged with 900 g of isopropyl alcohol, and 108.7 g of NaBH$_4$ was added with stirring in small portions. Under reflux with stirring was added dropwise 314.3 g of diethyl 2-octylmalonate obtained in (a) above, and 160 g of methanol was added dropwise. After completion of the dropwise addition, the reaction was effected for 2 hours. The reaction liquid was poured into 1.5 l of water, and concentrated hydrochloric acid was slowly added thereto with stirring for neutralization. After addition of 600 g of edible salt, the mixture was phase separated and the upper layer was separated.

To the so separated liquid was added a 10% aqueous KOH solution, and the mixture was refluxed with stirring for one hour and then cooled. After addition of edible salt, the mixture was extracted with isopropyl ether and the extract was washed with a saturated aqueous solution of edible salt. The solvent was distilled off and the residue was distilled under reduced pressure to obtain 145.1 g (yield 66.4%) of 2-octyl-1,3-propanediol.
GLC 98.3%
m.p. 48.0°–51.0° C.
b.p. 135° C./0.5 mmHg (c) Synthesis of $C_8H_{17}$-CH(CH$_2$Br)$_2$ A reaction vessel was charged with 145.1 g of 2-octyl-1,3-propanediol obtained in (b) above, and 283 g of phosphorus tribromide (PBr$_3$) was added dropwise with stirring at a temperature not exceeding 50° C. After the dropwise addition, the reaction was effected at 70° C. for 1 hour and then at 100° C. for 7 hours. The reaction solution was poured into ice water and the mixture was extracted with ether and the extract was washed with a dilute aqueous NaOH solution and then with water and dried over Glauber's salt. The solvent was distilled off and the residue was distilled under reduced pressure to obtain 163.2 g (yield 67.5%) of 2-octyl-1,3-dibromopropane.
GLC 97.5%
b.p. 96°–97° C./0.2 mmHg (d) Synthesis of

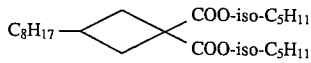

A reaction vessel was charged with 0.9 l of isopentyl alcohol, and 26.3 g of metallic sodium was added in small portions to dissolve the same in the alcohol. 166.4 g of diethyl malonate was added dropwise with stirring at 70° C. and the reaction was then effected under reflux with stirring for 1 hour. While distilling off the solvent, the temperature of the mixture was raised to about 130° C. By that point of time about 300 cc of the solvent had been distilled off. 163.2 g of 2-octyl-1,3-dibromopropane obtained in (c) above was added dropwise thereto and the reaction was effected for 7 hours.

The reaction liquid was concentrated under reduced pressure and the residue was poured into water. The mixture was extracted with benzene and the extract was washed with water and dried over Glauber's salt. The solvent was then distilled off and the residue was distilled under reduced pressure to obtain 99.4 g (yield 48.3%) of diisopentyl 3-octylcyclobutane-1,1-dicarboxylate.
GLC 86.1%
b.p. 145° C./0.3 mmHg (e) Synthesis of

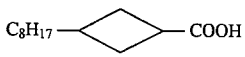

A reaction vessel was charged with 99.4 g of diisopentyl 3-octylcyclobutane-1,1-dicarboxylate obtained in (d) above and 350 ml of ethanol, and 500 g of 0.5% aqueous NaOH solution was added dropwise with stirring at room temperature. The mixture was refluxed with stirring until the disappearance of the starting material as confirmed by GLC (about 4 hours). To this reaction liquid was added dropwise 300 ml of concentrated hydrochloric acid, and the mixture was stirred at 60° C. for 30 minutes and then concentrated to a residual volume of 300 ml or less. The resultant concentrate was extracted with benzene added and the extract was filtered to remove insolubles. The benzene was distilled off to obtain crude 3-octylcyclobutane-1,1-dicarboxylic acid as residue.

The thus obtained residue was charged into a flask, and the temperature thereof was raised to around 170° C. so that decarboxylation took place. The mixture was distilled under reduced pressure, using a vaccum distillation apparatus, to obtain 48.4 g (yield 91.7%) of 3-octylcyclobutanecarboxylic acid.
b.p. 82°–130° C./23–140 mmHg (f) Synthesis of

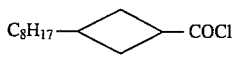

A reaction vessel was charged with 35 ml of benzene and 54 g of thionyl chloride, and 48.4 g of 3-octylcyclobutanecarboxylic acid obtained in (e) above under reflux with stirring to effect the reaction for 8 hours.

The solvent and the excess thionyl chloride were distilled off under reduced pressure, and the residue was distilled under reduced pressure to obtain 22.4 g (yield 42.5%) of 3-octylcyclobutanecarboxylic acid chloride.

(g) Synthesis of

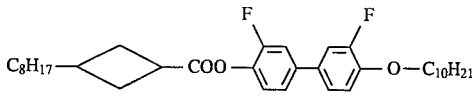

A reaction vessel was charged with 0.7 g of the crude 3,3'-difluoro-4-hydroxy-4'-decyloxybiphenyl obtained in Example 7-(c), 8 ml of pyridine and 14 ml of benzene. 0.5 g of 3-octylcyclobutanecarboxylic acid chloride obtained in (f) above was added dropwise with stirring at 60° C. and the mixture was refluxed with stirring for 5 hours. This reaction liquid was poured into water and the benzene layer was washed with water and dried over Glauber's salt. The benzene was distilled off and the residue was subjected to purification by column chromatography on silica gel (eluent: hexane/benzene=3/1), followed by preparative chromatography (YMC-PACK ODS SH-345-5; eluent: methanol), to obtain 0.45 g (yield 42.2%) of 3,3'-difluoro-4-decyloxybiphenyl-4'-yl 3-octylcyclobutanecarboxylate.

The purity of this product was at least 99% by HPLC and TLC showed only one spot. The resultant substance was confirmed to be the end product in view of its measurement by IR and its molecular ion peak found at 556 by Mass and also in view of the starting materials used.

The phase transition of this product was observed under a polarization microscope using a Mettler hot stage FP-82. A result of the observation is shown in Table 1.

EXAMPLE 10

(a) Synthesis of $C_4H_9$-CH(CH$_2$Br)$_2$

Except that 101.6 g of 2-butyl-1,3-propanediol was used in place of 145.1 g of 2-octyl-1,3-propanediol used in Example 9-(c), the operation was performed in the same manner as in Example 9-(c) to obtain 141.2 g (yield 71.1%) of 2-butyl-1,3-dibromopropane.
GLC 100.0%
b.p. 145°–155° C./60 mmHg (b) Synthesis of

Except that 134.2 g of 2-butyl-1,3-dibromopropane obtained in (a) above was used in place of 163.2 g of the 2-octyl-1,3-dibromopropane used in Example 9-(d), the operation was performed in the same manner as in Example 9-(d) to obtain 205.5 g (yield 78.5%) of diisopentyl 3-butylcyclobutane- 1,1-dicarboxylate.

GLC 89.8% b.p. 142.5°–148.0° C./1.0–1.6 mmHg (c) Synthesis of

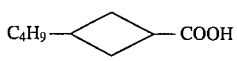

Except that 85.0 g of diisopentyl 3-butylcyclobutane-1,1-dicarboxylate obtained in (b) above was used in place of 99.4 g of the diisopentyl 3-octylcyclobutane-1,1-dicarboxylate used in Example 9-(e), the operation was performed in the same manner as in Example 9-(e) to obtain 29.7 g (yield 76.1%) of 3-butylcyclobutanecarboxylic acid.

GLC 97.7% b.p. 150°–160° C./35–45 mmHg (d) Synthesis of

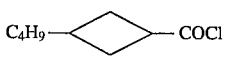

Except 35.9 g of 3-butylcyclobutanecarboxylic acid obtained in (c) above was used in place of 48.4 g of the 3-octylcyclobutanecarboxylic acid used in Example 9-(f), the operation was performed in the same manner as in Example 9-(f) to obtain 31.5 g (78.9%) of 3-butylcyclobutanecarboxylic acid chloride.

GLC 98.6% b.p. 90°–94° C./13 mmHg (e) Synthesis of

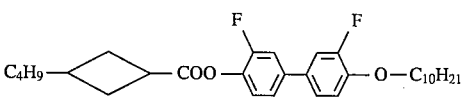

Except that 0.4 g of 3-butylcyclobutanecarboxylic acid chloride obtained in (d) above was used in place of 0.5 g of the 3-octylcyclobutanecarboxylic acid chloride used in Example 9-(g) and purification carried out by column chromatography on silica gel (hexane/benzene= 3/1) followed by preparative chromatography (YMC-PACK ODS SH- 345-5; eluent: methanol), the operation was performed in the same manner as in Example 9-(g) to obtain 0.38 g (yield 39.8%) of 3,3'-difluoro-4-decyloxybiphenyl-4'-yl 3-butylcyclobutanecarboxylate.

The purity of this product was at least 99% by HPLC and TLC showed only one spot. The resultant substance was confirmed to be the end product in view of its measurement by IR and its molecular ion peak found at 500 by Mass and also in view of the starting materials used.

The phase transition of this product was observed under a polarization microscope using a Mettler hot stage FP-82. A result of the observation is shown in Table 1.

EXAMPLE 11

Synthesis of

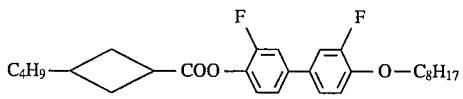

Except that 0.60 g of the crude 3,3'-difluoro-4-hydroxy-4'-octyloxybiphenyl obtained in Example 5-(c) was used in place of 0.7 g of the crude 3,3'-difluoro-4-hydroxy- 4'-decyloxybiphenyl used in Example 9-(g), 0.4 g of 3-butylcyclobutanecarboxylic acid chloride obtained in Example 10-(d) used in place of 0.5 g of the 3-octylcyclobutanecarboxylic acid chloride used in Example 9-(g) and purification carried out by way of column chromatography on silica gel (eluent: hexane/benzene=4/1), the operation was performed in the same manner as in Example 9-(g) to obtain 0.28 g (yield 30.9%) of 3,3'-difluoro- 4-octyloxybiphenyl-4'-yl 3-butylcyclobutanecarboxylate.

The purity of this product was at least 98% by HPLC and TLC showed only one spot. The resultant substance was confirmed to be the end product in view of its measurement by IR and its molecular ion peak found at 472 by Mass and also in view of the starting materials used.

The phase transition of this product was observed under a polarization microscope using a Mettler hot stage FP-82. A result of the observation is shown in Table 1.

EXAMPLE 12

(a) Synthesis of

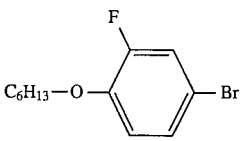

A reaction vessel was charged with 19.4 g of 2-fluoro-4-bromophenol, 16.8 g of hexyl bromide, 23.3 g of potassium carbonate and 510 ml of cyclohexanone and the reaction was effected with stirring at 120°–140° C. for 7 hours. The reaction liquid was poured into dilute hydrochloric acid and the mixture was extracted with benzene. The benzene layer was washed with water and dried over Glauber's salt, and the benzene was distilled off. The residue was purified by way of column chromatography on silica gel (eluent: hexane) to obtain 23.4 g (yield 83.6%) of 3-fluoro-4-hexyloxybromobenzene.

b.p. 120° C./0.5 mmHg (b) Synthesis of

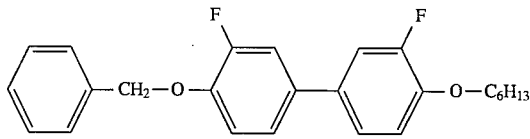

A reaction vessel was charged, under a nitrogen stream, with 0.24 g of magnesium and a small amount of iodine. A small portion of a solution of 2.1 g of 3-fluoro- 4-hexyloxybromobenzene obtained in (a) above in 10 ml of THF, and the mixture was warmed. After the start of the reaction, the remainder of the THF solution was added dropwise under reflux with stirring, and the mixture, after completion of the dropwise addition, was refluxed with stirring for 2 hours to prepare a Grignard reagent.

Another reaction vessel was charged with 0.4 g of $Cl_2Pd(PPh_3)_2$, then under a nitrogen stream, with 2.6 ml of a 1M solution of $(iso-C_4H_9)_2AlH$ in hexane, and then with a solution of 1.7 g of 2-fluoro-4-bromophenyl benzyl ether obtained in Example 4-(a) in 10 ml of THF.

The previously prepared Grignard reagent was added dropwise to the resultant mixture at 50°–60° C. and the reaction was effected with stirring at the same temperature for 2 hours. The reaction solution was poured into dilute hydrochloric acid and the mixture was extracted with benzene. The extract was washed with water and the solvent was distilled off. The residue was purified by way of column chromatography on silica gel (hexane/benzene=5/1→4/1→3/1) to obtain 1.8 g (yield 59.6%) of 3,3'-difluoro- 4-benzyloxy-4'-hexyloxybiphenyl.

HPLC 89.7%
m.p. 85 . 4°–93 . 7° C.
(c) Synthesis of

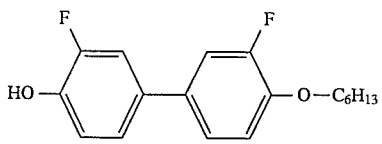

An autoclave was charged with a solution of 0.75 g of 3,3'-difluoro-4-benzyloxy-4'-hexyloxybiphenyl obtained in (b) above in 50 ml of ethyl acetate and 0.2 g of Pd/C (10%), the atmosphere in the reaction vessel was replaced with hydrogen. The mixture was stirred overnight at room temperature under a hydrogen pressure of 30 kg/cm². The reaction liquid was filtered to remove insolubles and the solvent was distilled off to obtain 0.6 g of crude 3,3'-difluoro- 4-hydroxy-4'-hexyloxybiphenyl. This crude product was directly used as starting material in the subsequent stage (d).
(d) Synthesis of

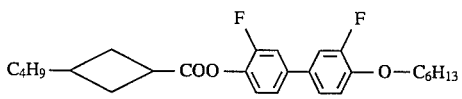

Except that the crude 3,3'-difluoro-4-hydroxy-4'-hexyloxybiphenyl obtained in (c) above was used in place of 0.7 g of the crude 3,3 '-difluoro-4-hydroxy-4'-decyloxybiphenyl and 0.4 g of 3-butylcyclobutanecarboxylic acid chloride obtained in Example 10-(d) in place of 0.5 g of the 3-octylcyclobutanecarboxylic acid chloride used in Example 9-(g), and purification was carried out by column chromatography on silica gel (eluent: hexane/benzene= 3/1) followed by preparative chromatography (YMC-PACK ODS SH- 345-5; eluent: methanol), the operation was performed in the same manner as in Example 9-(g) to obtain 0.33 g (yield 39.4%) of 3,3 '-difluoro-4 '-hexyloxybiphenyl-4-yl 3-butylcyclobutanecarboxylate.

The purity of this product was at least 99% by HPLC and TLC showed only one spot. The resultant substance was confirmed to be the end product in view of its measurement by IR and its molecular ion peak found at 444 by Mass and also in view of the starting materials used.

The phase transition of this product was observed under a polarization microscope using a Mettler hot stage FP-82. A result of the observation is shown in Table 1.

EXAMPLE 13

(a) Synthesis of $C_2H_5$-$CH(CH_2Br)_2$

Except that 83.2 g of 2-ethyl-1,3-propanediol was used in place of 145.1 g of the 2-octyl-1,3-propanediol used in Example 9-(c), the operation was performed in the same manner as in Example 9-(c) to obtain 145.8 g (yield 82.3%) of 2-ethyl-i, 3-dibromopropane.

GLC 96.5%
b.p. 72°–75° C./100 mmHg
(b) Synthesis of

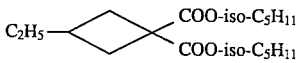

Except that 119.6 g of 2-ethyl-1,3-dibromopropane obtained in (a) above was used in place of 163.2 g of the 2-octyl-1,3-dibromopropane used in Example 9- (d), the operation was performed in the same manner as in Example 9-(d) to obtain 140.3 g (yield 86.5%) of diisopentyl 3-ethylcyclobutane-1,1-dicarboxylate.

GLC 86.7%
b.p. 100.0°–125.0° C./0.8 mmHg
(c) Synthesis of

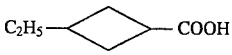

Except that 78.0 g of diisopentyl 3-ethylcyclobutane-1,1-dicarboxylate obtained in (b) above was used in place of 99.4 g of the diisopentyl 3-octylcylobutane-1,1-dicarboxylate used in Example 9-(e), the operation was performed in the same manner as in Example 9-(e) to obtain. 17.5 g (yield 54.7%) of 3-ethylcyclobutanecarboxylic acid.

GLC 97.8%
b.p. 150°–180° C./25–35 mmHg
(d) Synthesis of

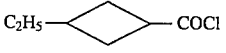

Except that 29.4 g of 3-ethylcyclobutanecarboxylic acid obtained in (c) above was used in place of 48.4 g of the 3-octylcyclobutanecarboxylic acid, used in Example 9-(f), the operation was performed in the same manner as in Example 9-(f) to obtain 12.4 g (yield 36.7%) of 3-ethylcyclobutanecarboxylic acid chloride.

GLC 98.0%
b.p. 72°–75° C./23 mmHg
(e) Synthesis of

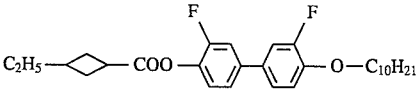

Except that 0.3 g of 3-ethylcyclobutanecarboxylic acid chloride obtained in (d) above was used in place of 0.5 g of the 3-octylcyclobutanecarboxylic acid chloride used in Example 9-(g) and purification was carried out by way of column chromatography on silica gel (hexane/benzene= 3/1), the operation was performed in the same manner as in Example 9-(g) to obtain 0.68 g (yield 75.5%) of 3,3'-difluoro-4-decyloxybiphenyl-4'-yl 3-ethylcyclobutanecarboxylate.

The purity of this product was at least 99% by HPLC and TLC showed only one spot. The resultant substance was confirmed to be the end product in view of its measurement by IR and its molecular ion peak found at 472 by Mass and also in view of the starting materials used.

The phase transition of this product was observed under a polarization microscope using a Mettler hot stage FP-82. A result of the observation is shown in Table 1.

EXAMPLE 14

Synthesis of

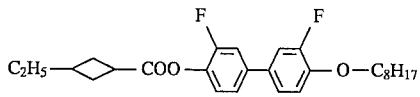

Except that 0.60 g of 3,3'-difluoro-4-hydroxy-4'-octyloxybiphenyl obtained in Example 5-(c) was used in place of 0.7 g of the crude 3,3'-difluoro-4-hydroxy-4'-decyloxybiphenyl and 0.3 g of 3-ethylcyclobutanecarboxylic acid chloride obtained in Example 13-(d) in place of 0.5 g of the 3-octylcyclobutanecarboxylic acid chloride used in Example 9-(g) and purification was carried out by way of column chromatography on silica gel (eluent: hexane/benzene=4/1), the operation was performed in the same manner as in Example 9-(g) to obtain 0.56 g (yield 30.9%) of 3,3'-difluoro-4-octyloxybiphenyl-4'-yl 3-ethylcyclobutanecarboxylate.

The purity of this product was at least 99% by HPLC and TLC showed only one spot. The resultant substance was confirmed to be the end product in view of its measurement by IR and its molecular ion peak at 444 by Mass and also in view of the starting materials used.

The phase transition of this product was observed under a polarization microscope using a Mettler hot stage FP-82. A result of the observation is shown in Table 1.

EXAMPLE 15

Synthesis of

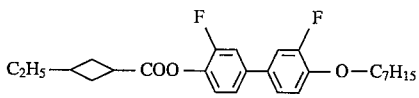

Except that 0.60 g of the crude 3,3'-difluoro-4-hydroxy-4'-heptyloxybiphenyl obtained in Example 6-(c) was used in place of 0.7 g of the crude 3,3'-difluoro-4-hydroxy- 4'-decyloxybiphenyl and 0.3 g of 3-ethylcyclobutanecarboxylic acid chloride obtained in Example 13-(d) in place of 0.5 g of the 3-octylcyclobutanecarboxylic acid chloride used in Example 9-(g) and purification was carried out by way of column chromatography on silica gel (eluent: hexane/benzene=2/1), the operation was performed in the same manner as in Example 9-(g) to obtain 0.74 g (yield 90.6%) of 3,3'-difluoro-4-heptyloxybiphenyl-4'-yl 3-ethylcyclobutanecarboxylate.

The purity of this product was at least 99% by HPLC and TLC showed only one spot. The resultant substance was confirmed to be the end product in view of its measurement by IR and its molecular ion peak found at 430 by Mass and also in view of the starting materials used.

The phase transition of this product was observed under a polarization microscope using a Mettler hot stage FP-82. A result of the observation is shown in Table 1.

EXAMPLE 16

(a) Synthesis of

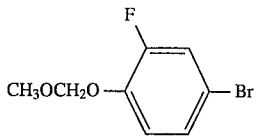

A reaction vessel was charged with 111 g of 2-fluoro-4-bromophenol and 700 ml of DMF, and 20 g of 70% sodium hydride was added with stirring at room temperature. The mixture was stirred at room temperature for 1 hour and 56 g of methoxymethyl chloride was then added dropwise. The mixture was stirred at room temperature for 3 hours. The reaction liquid was poured into dilute hydrochloric acid and the organic layer was extracted with benzene. The benzene layer was washed with water and dried over Glauber's salt. The benzene was distilled off and the residue was distilled under reduced pressure to obtain 110 g (yield 88%) of 3-fluoro-4-methoxymethoxybromobenzene.

GLC 98.1%
b.p. 84° C./1.0 mmHg
(b) Synthesis of

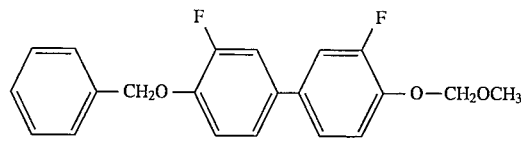

A reaction vessel was charged, under a nitrogen stream, with 5.5 g of magnesium and a small amount of iodine. A small portion of a solution of 50 g of 3-fluoro- 4-methoxymethoxybromobenzene obtained in (a) above in 200 ml of THF was added thereto and the mixture was warmed. After the start of the reaction, the remainder of the THF solution was added dropwise under reflux with stirring. After completion of the dropwise addition, the mixture was refluxed with stirring for 2 hours to prepare a Grignard reagent.

Another reaction vessel was charged with 2.0 g of Cl₂Pd(PPh₃)₂, then under a nitrogen stream with 30 ml of a 1M solution of (iso-C₄H₉)₂AlH in hexane and further with 200 ml of the solution of 64 g of 3-fluoro-4-benzyloxybromobenzene obtained in Example 4-(a) in THF.

The previously prepared Grignard reagent was added dropwise at 50°–60° C. to the mixture and the resultant mixture was reacted with stirring for 2 hours at the same temperature. The reaction liquid was poured into dilute hydrochloric acid and the mixture was extracted with benzene. After the extract was washed with water, the solvent was distilled off and the residue was recrystallized from n-hexane to obtain 68 g (yield 82%) of 3,3'-difluoro-4-benzyloxy-4'-methoxymethoxybiphenyl.

GLC 98.6%
(c) Synthesis of

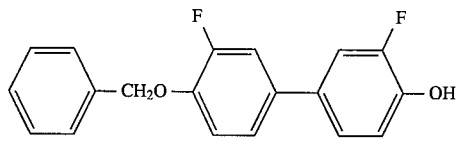

A reaction vessel was charged with 61 g of 3,3'-difluoro-4-benzyloxy-4'-methoxymethoxybiphenyl obtained in (b) above, 700 ml of methanol and 20 ml of hydrochloric acid, and the mixture was refluxed with stirring for 4 hours. The reaction liquid was concentrated and the residue was extracted with ether. The ether layer was washed with water and dried over Glauber's salt. The ether was distilled off and the resultant residue was recrystallized from methanol to obtain 41 g (yield 91%) of 3,3'-difluoro-4-benzyloxy-4'-hydroxybiphenyl.

GLC 97.4%

(d) Synthesis of

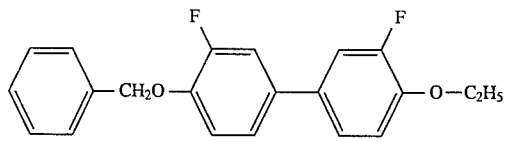

A reaction vessel was charged with 6.0 g of 3,3'-difluoro-4-benzyloxy-4'-hydroxybiphenyl obtained in (c) above, 2.5 g of ethyl bromide, 5.6 g of potassium carbonate and 120 ml of cyclohexanone, and the mixture was stirred at 120°–140° C. until the disappearance of the starting materials as confirmed by TLC (4 hours). The reaction liquid was poured into dilute hydrochloric acid and the mixture was extracted with benzene. The extract was washed with water and dried over Glauber's salt, and the solvent was distilled off. The residue was recrystallized from a benzene/hexane solvent mixture to obtain 6.1 g (yield 93.4%) of 3,3'-difluoro-4-benzyloxy-4'-ethoxybiphenyl.

GLC 99.6% m.p. 114.2°–114.7° C.

(e) Synthesis of

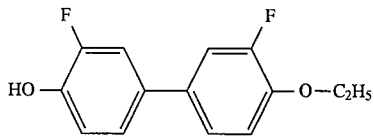

Except that 0.65 g of 3,3'-difluoro-4-benzyloxy-4'-ethoxybiphenyl obtained in (d) above was used in place of 0.75 g of the 3,3'-difluoro-4-benzyloxy-4'-hexyloxybiphenyl used in Example 12-(c), the operation was performed in the same manner as in Example 12-(c) to obtain crude 3,3'-difluoro- 4-hydroxy-4'-ethoxybiphenyl.

The crude product was directly used as starting material in the subsequent stage (f).

(f) Synthesis of

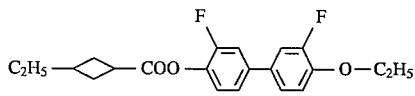

Except that 0.48 g of the crude 3,3'-difluoro-4-hydroxy-4'-ethoxybiphenyl obtained in (e) above was used in place of 0.7 g of the crude 3,3'-difluoro-4-hydroxy-4'-decyloxybiphenyl and 0.3 g of 3-ethylcyclobutanecarboxylic acid chloride obtained in Example 13-(d) in place of 0.5 g of the 3-octylcyclobutanecarboxylic acid chloride used in Example 9-(g) and purification was carried out by way of column chromatography on silica gel (eluent: hexane/benzene= 2/1), the operation was performed in the same manner as in Example 9-(g) to obtain 0.54 g (yield 78.7%) of 3,3'-difluoro- 4-ethoxy-4'-yl 3-ethylcyclobutanecarboxylate.

The purity of this product was at least 99% by HPLC, and TLC showed only one spot. The resultant substance was confirmed to be the end product in view of its measurement by IR and its molecular ion peak found at 360 by Mass and also in view of the starting materials used.

The phase transition of this product was observed under a polarization microscope using a Mettler hot stage FP-82. A result of the observation is shown in Table 1.

EXAMPLE 17

Synthesis of

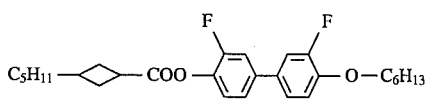

Except that 0.60 g of the crude 3,3'-difluoro-4-hydroxy-4'-hexyloxybiphenyl obtained in Example 12-(c) was used in place of 0.7 g of the crude 3,3'-difluoro-4-hydroxy-4'-decyloxybiphenyl and 0.4 g of 3-pentylcyclobutanecarboxylic acid chloride obtained in Example 1-(a) in place of 0.5 g of the 3-octylcyclobutanecarboxylic acid chloride used in Example 9-(g) and purification was carried out by way of column chromatography on silica gel (eluent: hexane/benzene=3/1), the operation was performed in the same manner as in Example 9-(g) to obtain 0.55 g (yield 65.5%) of 3,3'-difluoro-4-hexyloxybiphenyl-4'-Yl 3-pentylcyclobutanecarboxylate.

The purity of this product was at least 99% by HPLC, and TLC showed only one spot. The resultant substance was confirmed to be the end product in view of its measurement by IR and its molecular ion peak found at 458 by Mass and also in view of the starting materials used.

The phase transition of this product was observed under a polarization microscope using a Mettler hot stage FP-82. A result of the observation is shown in Table 1.

EXAMPLE 18

(a) Synthesis of

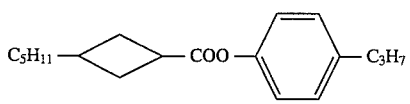

A reaction vessel was charged with 5.0 g of p-propylphenol, 18 ml of benzene and 130 ml of pyridine, and 7.0 g of 3-pentylcyclobutanecarboxylic acid chloride obtained in Example 1-(a) was added dropwise with stirring at room temperature. The mixture was reacted with stirring at the same temperature until TLC showed almost complete disappearance of the starting material p-propylphenol.

The reaction liquid was poured into water and the mixture was extracted with benzene. The extract was washed with water and dried over Glauber's salt. The solvent was distilled off and the residue was distilled under reduced pressure to obtain 7.7 g (yield 72.2%) of p-propylphenyl 3-pentylcyclobutanecarboxylate.

b.p. 180°–183° C./2 mmHg

HPLC 97.2% (cis form 47.5%, trans form 49.7%)

(b) Separation of cis and trans forms of

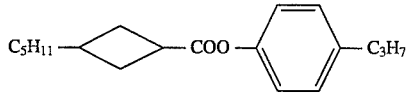

7.7 g of p-propylphenyl 3-pentylcyclobutanecarboxylate was separated by preparative chromatography into its cis and trans forms.

A separation apparatus, Prepbar Separating System 100 (E. Merck), was used under the following conditions: column: Lichrospher Si 60, 10 μm, 50 mm⌒×250 mm; detection wave length: UV 254 nm; eluent: hexane/IPE= 800/; and flow rate: 85 ml/min. After the solvents were distilled off, there were obtained 3.2 g of p-propylphenyl trans-3-pentylcyclobutanecarboxylate and 2.1 g of p-propylphenyl cis-3-pentylcyclobutanecarboxylate.

(c) Synthesis of trans

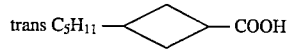

A reaction vessel was charged with 3.2 g of p-propylphenyl trans-3-pentylcyclobutanecarboxylate, 20 ml of ethanol and 20 ml of a 2M aqueous solution of $Na_2CO_3$, and the mixture was stirred under reflux for 10 hours.

The reaction liquid was applied to a glass column of 3 cm in diameter dry-packed with Extrelut (E. Merck) and allowed to stand for 20 minutes. About 200 ml of ether and then a dilute aqueous solution of NaOH were applied and the eluted aqueous solution was made acid with hydrochloric acid. The thus released oil was extracted with benzene and the extract was washed with water and dried over Glauber's salt. After the solvent was distilled off, there was obtained 1.8 g of crude trans-3-pentylcyclobutanecarboxylic acid.

(d) Synthesis of

A reaction vessel was charged with 10 ml of benzene, 2.5 g of thionyl chloride and 1.8 g of the crude trans-3-pentylcyclobutanecarboxylic acid obtained in (c) above, and the reaction was effected under reflux with stirring for 8 hours. The solvent and the excess thionyl chloride were distilled off under reduced pressure to obtain 1.8 g of residue (crude trans-3-pentylcyclobutanecarboxylic acid chloride). The residue was directly used as starting material in the subsequent stage.

(e) Synthesis of

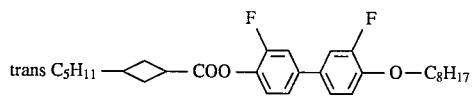

Except that 0.60 g of the crude 3,3'-difluoro-4-hydroxy-4'-octyloxybiphenyl obtained in Example 5-(c) was used in place of 0.7 g of the crude 3,3'-difluoro-4-hydroxy- 4'-decyloxybiphenyl and 0.4 g of the crude trans-3-pentylcyclobutanecarboxylic acid chloride obtained in (d) above in place of 0.5 g of the 3-octylcyclobutanecarboxylic acid chloride used in Example 9-(g) and purification was carried out by way of column chromatography on silica gel (eluent: hexane/benzene= 2/1), the operation was performed in the same manner as in Example 9-(g) to obtain 0.84 g (yield 91.1%) of 3,3'-difluoro-4-octyloxybiphenyl-4'-yl trans-3-pentylcyclobutanecarboxylate.

The purity of this product was 94.4% (cis form 3.9%) by HPLC. The resultant substance was confirmed to be the end product in view of its measurement by IR and its molecular ion peak found at 486 by Mass and also in view of the starting materials used.

The phase transition of this product was observed under a polarization microscope using a Mettler hot stage FP-82. A result of observation is shown in Table 1.

EXAMPLE 19

(a) Synthesis of

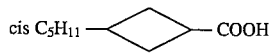

Except that 2.1 g of p-propylphenyl cis-3-pentylcyclobutanecarboxylate obtained in Example 18-(b) was used in place of 3.2 g of the p-propylphenyl trans-3-pentylcyclobutanecarboxylate used in Example 18-(c), the operation was performed in the same manner as in Example 18-(c) to obtain 1.2 g of cis-3-pentylcyclobutanecarboxylic acid.

(b) Synthesis of

Except that 1.2 g of cis-3-pentylcyclobutanecarboxylic acid obtained in (a) above was used in place of 1.8 g of the crude trans-3-pentylcyclobutanecarboxylic acid used in Example 18-(d), the operation was performed in the same manner as in Example 18-(d) to obtain 1.2 g of crude cis-3-pentylcyclobutanecarboxylic acid chloride.

(c) Synthesis of

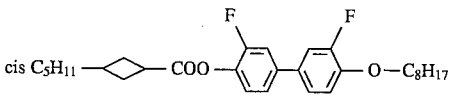

Except that 0.60 g of the crude 3,3'-difluoro-4-hydroxy-4'-octyloxybiphenyl obtained in Example 5-(c) was used in place of 0.7 g of the crude 3,3'-difluoro-4-hydroxy- 4'-decyloxybiphenyl and 0.4 g of cis-3-pentylcyclobutanecarboxylic acid chloride obtained in (b) above in place of 0.5 g of the 3-octylcyclobutanecarboxylic acid chloride used in Example 9-(g) and purification was carried out by way of column chromatography on silica gel (eluent: hexane/benzene= 2/1), the operation was performed in the same manner as in Example 9-(g) to obtain 0.58 g (yield 63.3%) of 3,3'-difluoro-4-octyloxybiphenyl-4'-yl cis-3-pentylcyclobutanecarboxylate.

The purity of this product was 92.2% (trans form 7.4%) by HPLC. The resultant substance was confirmed to be the end product in view of its measurement by IR and its molecular ion peak found at 486 by Mass and also in view of the starting materials used.

The phase transition of this product was observed under a polarization microscope using a Mettler hot stage FP-82. A result of the observation is shown in Table 1.

EXAMPLE 20

Three different compounds obtained in the corresponding Examples were mixed in the following weight ratio. The mixture was inserted into a Mettler hot stage FP-82 and its phase transition was observed under a polarization microscope.

| | | Ratio by weight |
|---|---|---|
| $C_5H_{11}$—⟨⟩—COO—⟨⟩—⟨⟩(F)—O—$C_8H_{17}$ | (Compound of Example 2) | 2 |
| $C_5H_{11}$—⟨⟩—COO—⟨⟩(F)—⟨⟩—O—$C_8H_{17}$ | (Compound of Example 3) | 1 |
| $C_5H_{11}$—⟨⟩—COO—⟨⟩(F)—⟨⟩(F)—O—$C_8H_{17}$ | (Compound of Example 5) | 2 |

As a result, there were observed, as the temperature increases, transitions from crystalline to SmC phase at 14.2° C., from SmC to Ne phase at 60.9° C. and from Ne phase to isotropic liquid at 65.3° C.

There was thus obtained a mixture showing the SmC phase over a wide temperature range including room temperature.

EXAMPLE 21

A ferroelectric liquid crystalline composition was prepared by mixing 90% by weight of the mixed crystals prepared in Example 20 with 10% by weight of the following ferroelectric substance known in the art:

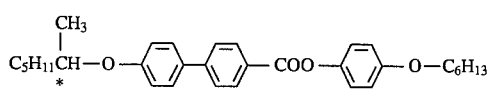

(Liquid crystalline substance known in the art)

This liquid crystalline composition was found to show, as the temperature decreases, phase transitions from isotropic liquid to Ch phase at 67° C. and from Ch phase to SmC* phase at 60° C.

A 3 μm-thick liquid crystalline cell, provided with transparent electrodes, was prepared by subjecting the polyvinyl alcohol (PVA)-coated surface to a parallel aligning treatment by rubbing. The previously prepared ferroelectric liquid crystalline composition was enclosed in this liquid crystalline cell and gradually cooled from the isotropic liquid to SmC* phase to prepare a liquid crystal element. This liquid crystal element was interposed between two polarization panels and a voltage was applied thereto. Response times were determined from changes in intensity of transmission light.

The response time upon application of a 200 Hz square wave of ±10 V at 50° C. was found to be 572 μsec.

EXAMPLE 22

A ferroelectric liquid crystalline composition was prepared by mixing compound (a) obtained in Example 18 with the optical active compound (c) obtained in Synthetic Example as will be described below in the following ratio:

| | | |
|---|---|---|
| (a) | $C_5H_9$—⟨⟩—COO—⟨⟩(F)—⟨⟩(F)—O—$C_8H_{17}$ | 90 wt % |
| (c) | $C_6H_{13}\overset{*}{C}HCH_2$—O—⟨⟩(F)—⟨⟩—O—$C_8H_{17}$ (with F substituent) | 10 wt % |

This composition was injected into a 3 μm gap liquid crystal cell, prepared from a polyimide-coated, rubbed glass substrate provided with transparent electrodes, to prepare a liquid crystal element. This liquid crystal element was interposed between two polarization plates. The response time upon application of a 200 Hz square wave of +5 V-μm was determined from the change in intensity of transmission light to be 95 μsec (60° C.).

Phase transition temperatures of the ferroelectric liquid crystalline composition prepared above was as follows:

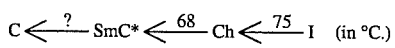

EXAMPLE 23

A ferroelectric liquid crystalline composition was prepared by mixing compound (b) obtained in Example 19 with the optical active compound (c) obtained in Synthetic Example as will be described below in the following ratio:

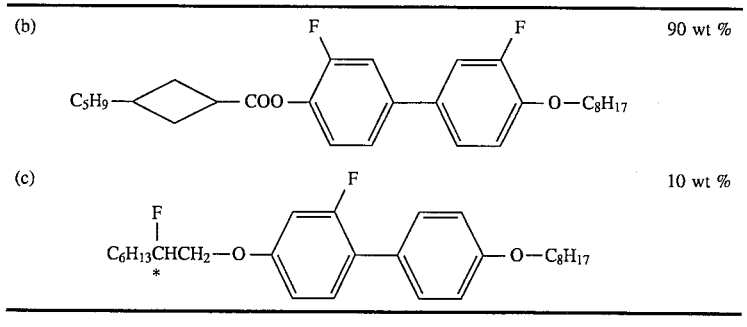

The response time for the thus prepared ferroelectric liquid crystalline composition was determined in the same manner as in Example 22 to be 95 μsec (44° C.).

Phase transition temperatures of the ferroelectric liquid crystalline composition were as follows:

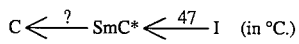

As can be seen from these examples, the compounds of the present invention are useful as SmC base mixtures in the preparation of ferroelectric liquid crystalline compositions showing high speed response.

Synthetic Example (a) Synthesis of

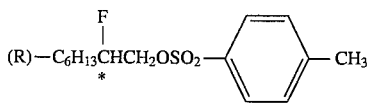

A reaction vessel was charged with 10.0 g of (2R)-2fluorooctanol and 25 ml of pyridine, and 13.0 g of tosyl chloride was added with stirring at 0°–5° C. After the reaction was effected for 6 hours, the mixture was poured into water and extracted with 100 ml of benzene. The resultant solution in benzene was washed sequentially with water, an aqueous solution of $NaHCO_3$ and water in that order, and dried over Glauber's salt. The solvent was distilled off to obtain 19.0 g (yield 92.6%) of crude (2R)-2-fluorooctyl tosylate as the residue.

GLC 90.8%

(b) Synthesis of

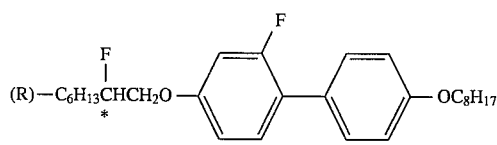

A reaction vessel was charged with 2.0 g of (2R)-2-fluorooctyl tosylate obtained in (a) above, 2.1 g of 2-fluoro-4-hydroxy-4'-octyloxybiphenyl, 1.8 g of potassium carbonate and 20 ml of cyclohexanone, and the mixture was heated at 140° C. with stirring for 6 hours. The reaction liquid was poured into dilute hydrochloric acid and the mixture was extracted with ether. The extract was washed with water and dried over Glauber's salt, and the solvent was distilled off. The residue was refluxed in alumina/hexane for 1 hour for decolorization. The alumina was filtered off and the hexane was distilled off. The residue was recrystallized from acetone to obtain 2.0 g (yield 67.7%) of (R) -2-fluoro-4-(2-fluorooctyl)oxy-4'-octyloxybiphenyl.

The purity of this product was 99.5% by HPLC and the resultant substance was confirmed to be the end product in view of its measurement by IR and its molecular ion peak found at 446 by Mass and also in view of the starting materials used.

The phase transition of this product was observed under a polarization microscope provided with a Mettler hot stage FP-82. A result of the observation is shown in the following:

| C | SmA | Ch | I |
|---|---|---|---|
| · 38.5 | (· 60.7) | · 62.7 | · (in °C.) |

TABLE 1

Phase transition temperature of compound $R^1$—◇—COO—⬡—⬡—O—$R^2$ (in °C.)

| Example No. | $R^1$ | $X^1$ | $X^2$ | $X^3$ | $X^4$ | $R^2$ | C | Sx | Sc | SA | Ne | I |
|---|---|---|---|---|---|---|---|---|---|---|---|---|
| 1 | $C_5H_{11}$ | H | H | H | H | $C_8H_{17}$ | · ? | · 109 | · Sb 117 | | | · |
| 2 | " | H | H | H | F | " | · 72.0 | | (· 61.0) | · 87.0 | | · |
| 3 | " | H | F | H | H | " | · 11.0 | | · 25.0 | | · 60.6 | · |

TABLE 1-continued

Phase transition temperature of compound 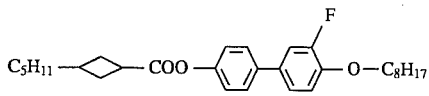 (in °C.)

| Example No. | R¹ | X¹ | X² | X³ | X⁴ | R² | C | Sx | Sc | SA | Ne | I |
|---|---|---|---|---|---|---|---|---|---|---|---|---|
| 4 | " | F | H | H | H | " | · ? | · 64.6 | · 80.4 | | | · |
| 5 | " | F | H | H | F | " | · 23.0 | | · 59.0 | | | · |
| 6 | " | F | H | H | F | $C_7H_{15}$ | · ? | · 11.5 | · 57.0 | | | · |
| 7 | " | F | H | H | F | $C_{10}H_{21}$ | · 2.5 | | · 65.3 | | | · |
| 8 | H | F | H | H | F | " | · 52.5 | | · | (· 19.5) | (· 29.0) | · |
| 9 | $C_8H_{17}$ | F | H | H | F | $C_{10}H_{21}$ | · 32.1 | | · 66.3 | | | · |
| 10 | $C_4H_9$ | F | H | H | F | " | · 4.6 | | · 63.9 | | | · |
| 11 | " | F | H | H | F | $C_8H_{17}$ | · −9.3 | | · 61.1 | | · 63.6 | · |
| 12 | " | F | H | H | F | $C_6H_{13}$ | · −3* C' | | · 40.0 | | · 47.0 | · |
| 13 | $C_2H_5$ | F | H | H | F | $C_{10}H_{21}$ | · 8* | · 28* C' | · 52.8 | · 53.7 | · 56.6 | · |
| 14 | " | F | H | H | F | $C_8H_{17}$ | · −2* | · 17* | · 49.6 | | · 56.5 | · |
| 15 | " | F | H | H | F | $C_7H_{15}$ | · 4.3 | | · 42.3 | | · 44.5 | · |
| 16 | " | F | H | H | F | $C_2H_5$ | · 60.2 C' | | | | (· 28.1) | · |
| 17 | $C_5H_{11}$ | F | H | H | F | $C_6H_{13}$ | · −4.5 | · 13.5 | · 49.5 | | · 53.8 | · |
| 18 | " | F | H | H | F | $C_8H_{17}$ | · 29.0 | | · 72.4 | | · 80.3 | · |
| 19 | " | F | H | H | F | " | · 15.8 | | · 48.0 | | | · |

Temperatures with * are readings from DSC

We claim:

1. An optically inactive cyclobutanecarboxylic acid derivative of formula (I)

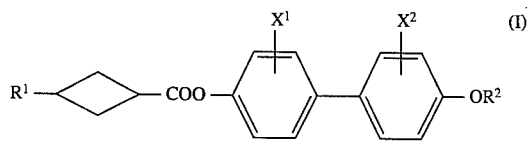

wherein R¹ is a straight chain alkyl group having 1–14 carbon atoms, R² is a straight chain alkyl group having 1–14 carbon atoms, and

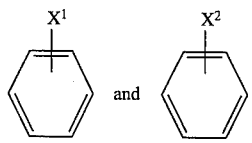

independently represent monofluoro-substituted 1,4-phenylene or difluoro-substituted 1,4 phenylene, wherein said optically inactive cyclobutanecarboxylic acid derivative exhibits a smectic C phase over a range of at least 24.8 degrees Centigrade.

2. The cyclobutanecarboxylic acid derivative as claimed in claim 1, wherein the compound of the general formula (I) is in the trans form.

3. The cyclobutanecarboxylic acid as claimed in claim 1, wherein the compound of the general formula (I) is in the cis form.

4. The cyclobutanecarboxylic acid derivative as claimed in claim 1, wherein the compound of the general formula (I) is:

$C_5H_{11}$—◇—COO—⬡—⬡—O—$C_8H_{17}$ (with F)

5. The cyclobutanecarboxylic acid derivative as claimed in claim 1, wherein the compound of the general formula (I) is:

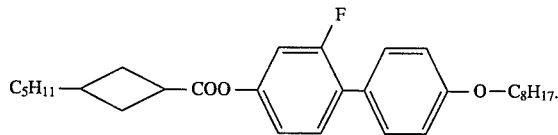

6. The cyclobutanecarboxylic acid derivative as claimed in claim 1, wherein the compound of the general formula (I) is:

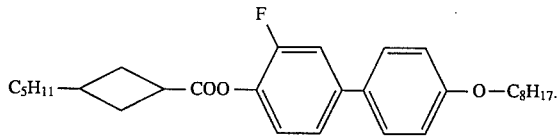

7. The cyclobutanecarboxylic acid derivative as claimed in claim 1, wherein the compound of the general formula (I) is:

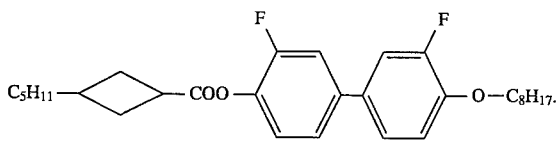

8. The cyclobutanecarboxylic acid derivative as claimed in claim 1, wherein the compound of the general formula (I) is:

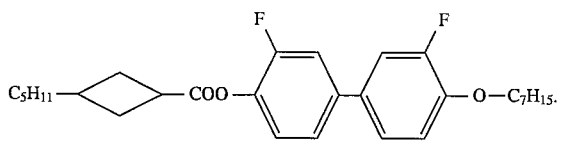

9. The cyclobutanecarboxylic acid derivative as claimed in claim 1, wherein the compound of the general formula (I) is:

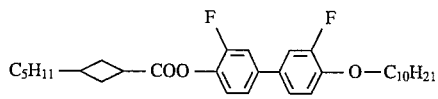

10. The cyclobutanecarboxylic acid derivative as claimed in claim 1, wherein the compound of the general formula (I) is:

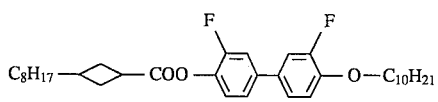

11. The cyclobutanecarboxylic acid derivative as claimed in claim 1, wherein the compound of the general formula (I) is:

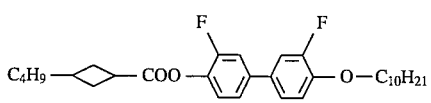

12. The cyclobutanecarboxylic acid derivative as claimed in claim 1, wherein the compound of the general formula (I) is:

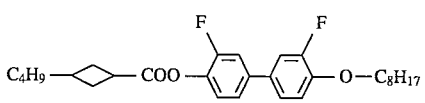

13. The cyclobutanecarboxylic acid derivative as claimed in claim 1, wherein the compound of the general formula (I) is:

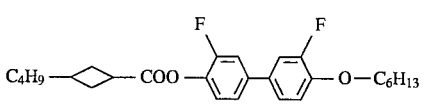

14. The cyclobutanecarboxylic acid derivative as claimed in claim 1, wherein the compound of the general formula (I) is

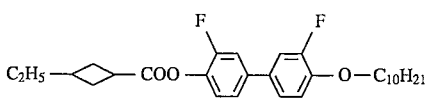

15. The cyclobutanecarboxylic acid derivative as claimed in claim 1, wherein the compound of the general formula (I) is:

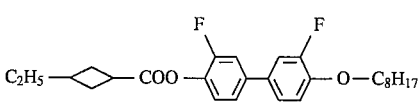

16. The cyclobutanecarboxylic acid derivative as claimed in claim 1, wherein the compound of the general formula (I) is:

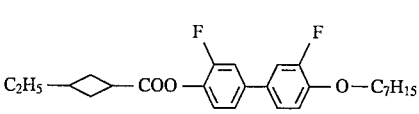

17. The cyclobutanecarboxylic acid derivative as claimed in claim 1, wherein the compound of the general formula (I) is:

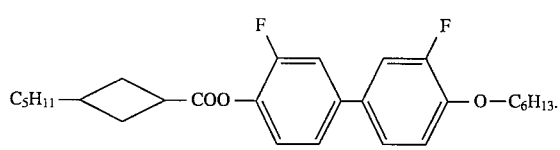

18. The cyclobutanecarboxylic acid derivative as claimed in claim 1, wherein the compound of the general formula (I) is:

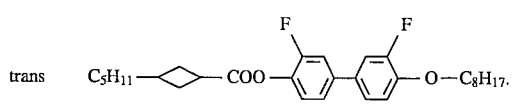

19. The cyclobutanecarboxylic acid derivative as claimed in claim 1, wherein the compound of the general formula (I) is:

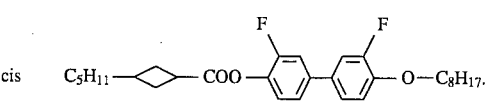

* * * * *

UNITED STATES PATENT AND TRADEMARK OFFICE
CERTIFICATE OF CORRECTION

PATENT NO. : 5,545,747
DATED : August 13, 1996
INVENTOR(S) : Megumi KAWAGUCHI et al.

It is certified that error appears in the above-indentified patent and that said Letters Patent is hereby corrected as shown below:

On the title page, Item [21] Appl. No., please insert the following:

--[22] PCT Filed: Aug. 16, 1991
  [86] PCT No.: PCT/JP91/01097
       371 Date: Apr. 16, 1992
       102(e) Date: Apr. 16, 1992--

Signed and Sealed this

Twenty-second Day of April, 1997

Attest:

BRUCE LEHMAN

*Attesting Officer*

*Commissioner of Patents and Trademarks*